(12) United States Patent
Bellantone

(10) Patent No.: US 10,140,426 B2
(45) Date of Patent: Nov. 27, 2018

(54) METHOD FOR PREDICTING THE SOLUBILITY OF A MOLECULE IN A POLYMER AT A GIVEN TEMPERATURE

(71) Applicant: Robert A. Bellantone, Yonkers, NY (US)

(72) Inventor: Robert A. Bellantone, Yonkers, NY (US)

( * ) Notice: Subject to any disclaimer, the term of this patent is extended or adjusted under 35 U.S.C. 154(b) by 0 days.

(21) Appl. No.: 15/732,529

(22) Filed: Nov. 21, 2017

(65) Prior Publication Data
US 2018/0089399 A1   Mar. 29, 2018

Related U.S. Application Data

(62) Division of application No. 14/121,424, filed on Sep. 4, 2014.

(60) Provisional application No. 61/960,236, filed on Sep. 14, 2013.

(51) Int. Cl.
| | |
|---|---|
| *G01N 25/00* | (2006.01) |
| *G01K 17/00* | (2006.01) |
| *G06F 19/00* | (2018.01) |
| *G01N 33/15* | (2006.01) |

(52) U.S. Cl.
CPC ......... *G06F 19/704* (2013.01); *G01N 25/005* (2013.01); *G01N 33/15* (2013.01)

(58) Field of Classification Search
USPC ........................................ 374/43, 31, 35, 10
See application file for complete search history.

(56) References Cited

U.S. PATENT DOCUMENTS

| | | | |
|---|---|---|---|
| 6,193,413 B1 * | 2/2001 | Lieberman | G01K 17/006 374/43 |
| 2006/0036069 A1 * | 2/2006 | Kooi | G01J 5/58 528/499 |
| 2009/0092169 A1 * | 4/2009 | Hallen | G01N 25/18 374/33 |

* cited by examiner

*Primary Examiner* — Mirellys Jagan
(74) *Attorney, Agent, or Firm* — Jean B. Mauro

(57) ABSTRACT

The invention provides an improved method to predict the solubility of a drug or other molecule in a solid polymer or other matrix at any temperature. The instant invention provides a method to determine the difference in specific enthalpy, specific entropy and specific Gibbs energy between a solid solution and the unmixed components, as well as a method to use those data to predict the solubility of a drug or other molecule in a solid polymer or other matrix. The method uses known thermodynamics equations and thermal analysis data, such as obtained from DSC (differential scanning calorimetry) at temperatures that are lower than the temperature at which the solubility is predicted. The method allows prediction of the drug-in-polymer solubilities without the use of elevated temperatures, but still avoids impractically long experiments. The instant invention can predict the solubility at many temperatures, but is particularly useful in the pharmaceutical sciences to predict the solubility of a drug in a polymer at typical storage temperatures, which are typically near room temperature or below.

3 Claims, 4 Drawing Sheets

Change in Gibbs energy $\Delta G_{SS}$ per gram of polymer vs. drug weight fraction.

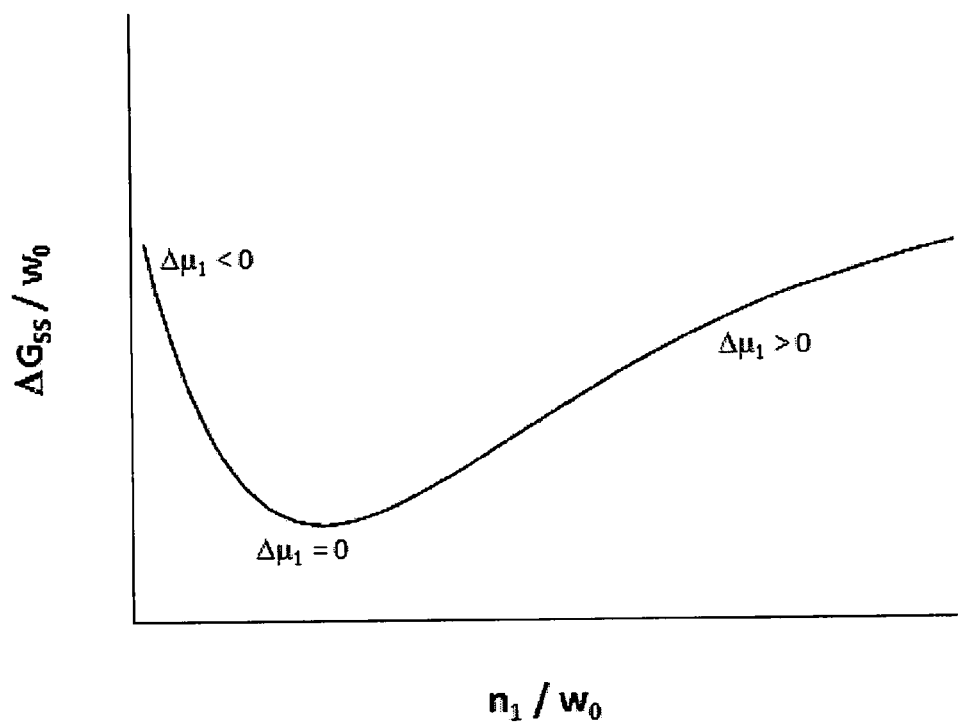
Figure 1. Hypothetical plot of $\Delta G_{SS}$ vs. moles of drug (both per gram of polymer).

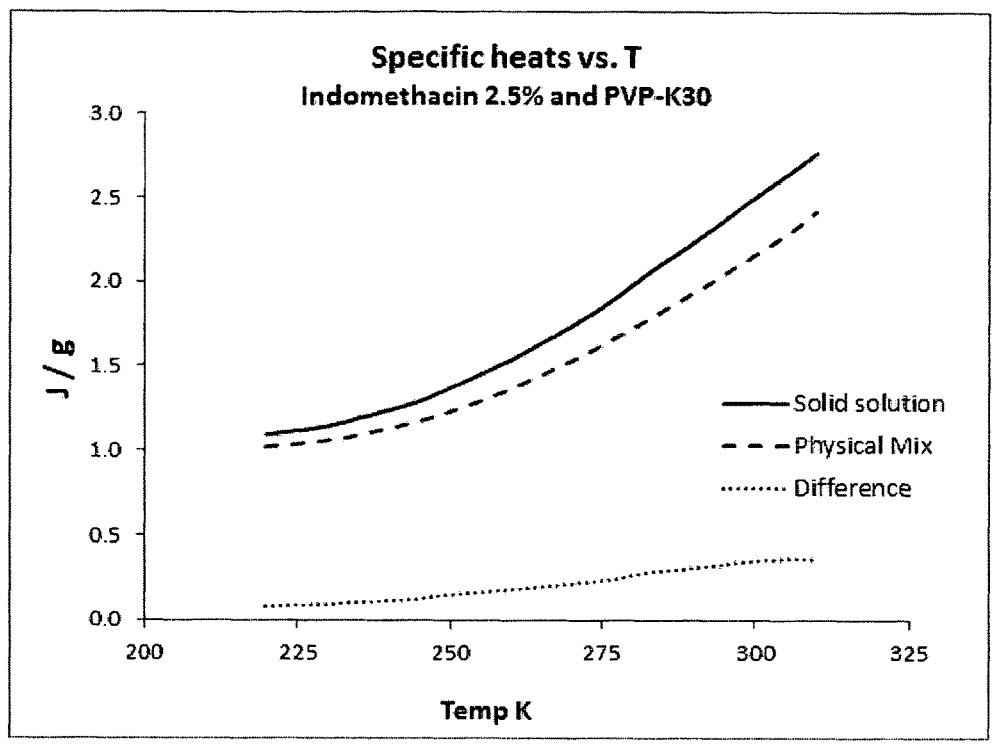
Figure 2. Specific heat vs. temperature of indomethacin 2.5% in PVP-K30.

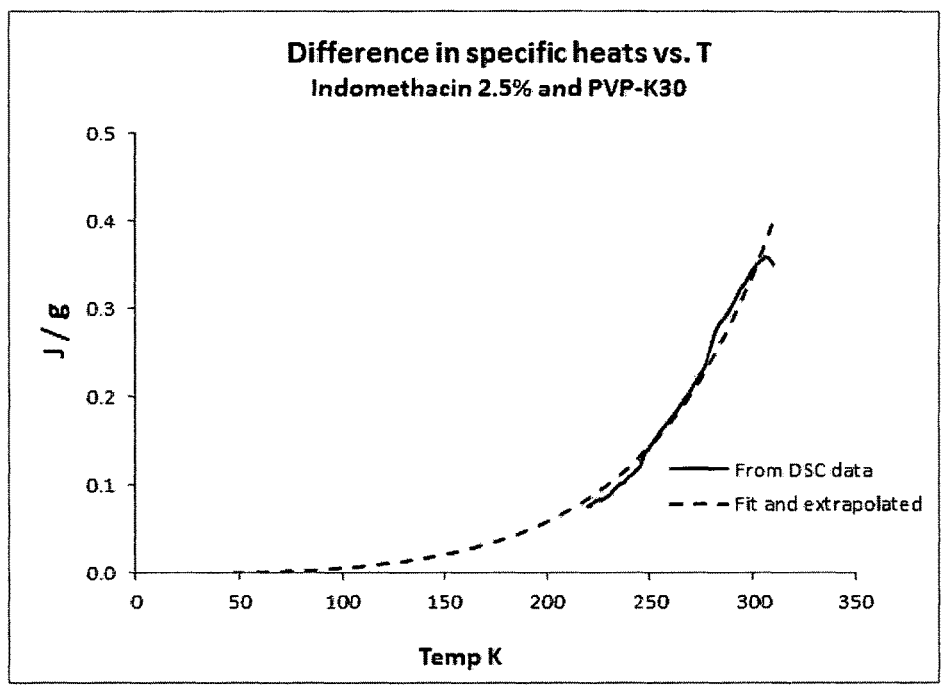
Figure 3. Specific heat difference between a solid solution and unmixed components for indomethacin 2.5% and PVP-K30 from Example 1.

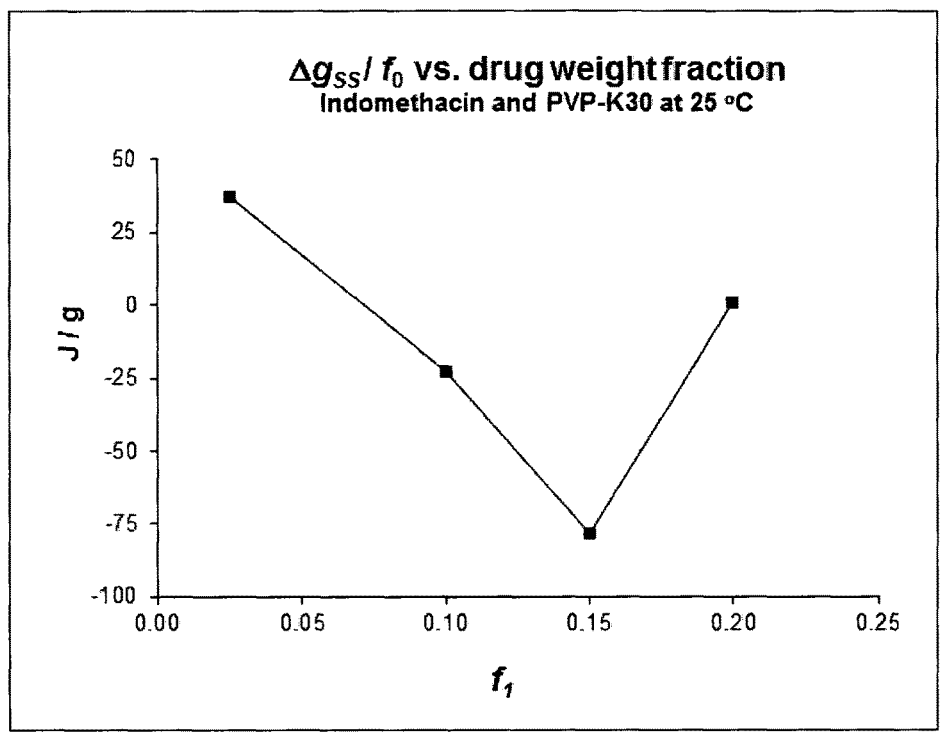
Figure 4. Change in Gibbs energy ΔGss per gram of polymer vs. drug weight fraction.

METHOD FOR PREDICTING THE SOLUBILITY OF A MOLECULE IN A POLYMER AT A GIVEN TEMPERATURE

BACKGROUND OF THE INVENTION

Field of the Invention

In the following, numbers in square brackets refer to items in the reference list. For instance, [1] refers to Reference #1, etc.

One of the most important problems facing pharmaceutical scientists is to orally deliver drugs with poor aqueous solubility. This is because drugs must dissolve in GI fluids before they can be absorbed across membranes into the bloodstream, and poorly soluble drugs may not dissolve in sufficient amounts to provide a therapeutic dose to the patient. Several strategies have been identified over the years to address this problem, including formulating drugs as amorphous solid forms. Amorphous solids typically dissolve faster than crystalline forms in GI fluids, and can also produce supersaturated solutions in which the dissolved drug concentration exceeds the thermodynamic solubility. Since diffusion rates across membranes typically increase as the dissolved concentration in GI fluids increases, producing higher dissolved drug concentrations can help to increase the rate and extent of drug absorption into the bloodstream.

The term crystalline refers to the drug or polymer with some long range order, or regular pattern of molecular packing. (For some substances, it is possible to have more than one crystalline form because more than one such regular arrangement can occur.) The term amorphous refers to the drug or polymer with irregular packing and no long range order. These terms and concepts are taken in the standard sense as understood by one of ordinary skill in the art [1]. A substance that is referred to as crystalline refers to a substance that is purely in one crystalline form, with no amorphous regions or other crystalline forms present. A substance that is referred to as amorphous refers to a substance that is purely amorphous, with no crystalline forms of any type present. However, a substance cannot be verified as being purely in one crystalline form or purely amorphous because instruments, such as X-ray diffraction and differential scanning calorimetry, have limits of detection and may not be able to detect levels of other crystalline or amorphous regions that fall below those limits. Thus, it is understood that a crystalline substance refers to one that is substantially in one crystalline form within the limits of detection of instruments. Similarly, an amorphous substance is one that shows no crystalline forms within the limits of detection of instruments.

One approach to produce amorphous forms of drugs is to dissolve the drug in a solid material (also referred to as a matrix) to create what is known as a solid solution, also referred to as an amorphous solid dispersion or a solid dispersion. The term solution refers to a molecular mixture or dispersion of two or more components that is homogenous and forms a one-phase system [1]. (In some reports, solid dispersions have also been defined as dispersions of drug molecules and small drug particles. In this document, unless otherwise noted, the term solid dispersion will be taken to mean solid solution.) In typical pharmaceutical applications, a drug is dispersed and the solid matrix is made of a polymer or mixture of polymers, which acts as a solid solvent medium.

Solid solutions are distinct from the unmixed components because mixing on a molecular level allows the drug-polymer interactions to become significant. The term unmixed components refers to a mixture of drug and polymer particles, in which the drug and polymer are not mixed or substantially not mixed on a molecular scale. This is sometimes used interchangeably with the term physical mixture, which refers to a mixture of macroscopic particles of drug and macroscopic particles of polymer, in which the particles are large enough so there is substantially no molecular mixing and the effects of drug-polymer interactions can be neglected.

Solid solutions can be formed in several ways. For instance, it is possible to melt the drug and polymer, then mix the two, and finally reduce the temperature to room temperature. Alternatively, the drug and polymer can be dissolved in a common liquid solvent, which is then evaporated to leave a solid solution. These methods are implemented in techniques such as hot melt extrusion and spray drying. However, if solutions made by different methods are identical on a molecular scale, then they will have identical properties.

If the dissolved concentration of drug in the polymer is lower than a concentration referred to as the solubility (also referred to as the saturation concentration) of the drug in the solid polymer, the individual molecules tend to remain in solution, meaning they stay dispersed and do not tend to aggregate into clusters or particles. In this case, the solid solution is said to be physically stable, and the dissolved concentration is said to be below the saturation concentration. On the other hand, if the dissolved concentration of drug in the polymer is higher than solubility of the drug in the polymer, there is a thermodynamic tendency for the molecules to aggregate and form clusters or particles, which is also referred to as precipitation. In this case, the solid solution is said to be supersaturated and the solid solution is unstable (or physically unstable). The solubility is the maximum dissolved concentration of a drug in a polymer that is stable and does not tend to precipitate. The solubility of a drug in a polymer depends on the temperature, and generally increases with increasing temperature. It also depends on the pressure, but in typical applications of pharmaceutical interest the pressure can be taken as one atmosphere, but this is not required theoretically.

If a supersaturated solid solution is allowed to stand, the drug molecules will aggregate and undergo some amount of precipitation that results in some loss of mixing on the molecular level. If allowed to stand for an infinite time, a final equilibrium state will be reached in which the drug is dissolved in the polymer at a concentration equal to its solubility, and the remaining drug molecules will have precipitated as clusters and particles of drug molecules. While standing for an infinite time is not achieved in practice, the equilibrium state is of theoretical importance because it indicates the state to which a supersaturated solid solution tends over time.

Solid solution drug formulations can produce faster drug dissolution and create supersaturation in GI fluids, which can increase the rates and extents of absorption of poorly soluble drugs. Typically, increasing the dissolved drug concentration in the polymer will increase the dissolution rate and maximum dissolved concentration in GI fluids. In addition, increasing the drug concentration in the polymer potentially allows smaller tablets or capsules to be formulated. Thus, it is often desirable to increase the dissolved drug concentration in the solid polymer and produce supersaturated solid solutions, but this can lead to unstable solid solutions and a tendency towards precipitation. Precipitation is usually undesirable because it reduces the dissolved concentration of drug in the polymer, which typically results in a loss of the solubility and dissolution benefits in the GI fluids gained by forming the solid solution.

Because increasing the dissolved drug concentration in the polymer can help to improve drug absorption while increasing it too much creates a tendency to precipitate, it is of interest to know the highest stable drug concentration that can be dissolved in a polymer, which is the same as the drug solubility in the polymer. Surprisingly, despite the importance of knowing the drug solubility in a polymer, no standard method exists to determine or predict it, and it is especially challenging to experimentally determine the drug-in-polymer solubility at room temperature or below. This is because the mobility of the drug molecules in polymers of interest is usually low at room temperature, so the migration of drug molecules towards each other, along with subsequent nucleation and precipitation, takes a long time. Thus, experimental solubility determinations done at room temperature could take months, years or even decades to complete.

The instant invention provides a method of determining or predicting the solubility of molecules in solid matrices. One application of pharmaceutical interest is to predict the solubility of drugs in solid polymers. The invention relates the use of thermal analysis methods such as differential scanning calorimetry (DSC) together with published equations in a procedure to predict the drug solubility in the polymer without the need to actually wait for the equilibration of the solution to occur. Waiting for an equilibration to occur is sometimes possible experimentally at elevated temperatures, but is often impractical at or near room temperature because it may take many years for such equilibration to occur. Thus, the invention provides important information of interest to drug formulators and other scientists.

While the primary uses of the instant invention discussed in this document are related to the pharmaceutical sciences, the invention is not limited to that field. Within the pharmaceutical sciences, a typical application would be in designing oral dosage forms in which a solid solution is formed by dissolving a drug with poor solubility in GI fluids in a polymer. Typically, the dispersed molecule would be a drug with a molecular weight of less than 1500 Daltons However, it may also include groups of two or more molecules, such as co-crystals or other coordinates, and larger molecules such as other polymers, proteins and other biological molecules. Also, while the solid matrix is typically a polymer, the invention is not limited to polymers and may be applied to any solid material in which the drug or other molecule can be dissolved. In addition, at the given temperature, the matrix can be a solid (above, at or below the glass transition temperature Tg if applicable). The matrix may also be a viscous liquid, or a semi-solid. Further, the solid material could be in different forms at different temperatures, such as a solid at one temperature and a viscous liquid at another.

It is known that the solubility of a drug in a solid matrix depends on the temperature. An important feature of the invention is that the solubility can be predicted at many temperatures. This is important when considering the solubility at temperatures corresponding to storage temperatures. For instance, depending on the local climate and availability of heating and cooling in homes, a storage temperature can range from less than 20° C. to more than 35° C. If refrigerated, the storage temperature would be even lower. Thus, one important use of this invention is to predict the solubility of a drug in a polymer at various storage temperatures. However, the instant invention is not limited to the range of temperatures corresponding to storage temperatures, but can also be applied at higher and lower temperatures.

SUMMARY OF THE PRIOR ART

It is well known that formulating drugs as solid solutions in a matrix such as a solid polymer can facilitate faster dissolution and increased bioavailability [2-4]. In practice, it is sometimes desirable to formulate solid solutions for which the dissolved drug concentration is higher than its solubility in the polymer, which can improve the dissolution and bioavailability benefits, and also minimize the physical size of tablets or capsules to make them easier to swallow. However, if the dissolved drug concentration is greater than its solubility in the polymer, precipitation of the drug in the polymer will be thermodynamically favored. Precipitation is undesirable because it typically reduces the solubility/dissolution benefits gained by making the solid solution formulation [5]. Thus, it is of interest to know the solubility of the drug-in-polymer, which represents the maximum stable concentration of dissolved drug in the polymer.

The solubility of a drug in a polymer depends on a number of factors, such as the pressure, temperature and chemical properties of the drug and polymer. Most discussions in the literature have been related to the chemical properties and are analogous to the classical Hildebrand and Scott theory of real solutions [6]. For instance, solubility parameters have been calculated and related to interaction parameters characterizing the relative molecular interactions of the drug and polymer [7, 8]. In turn, these interaction parameters are used with the Flory-Huggins model to calculate the enthalpy of mixing and the entropy of mixing of the drug in the polymer [9]. In some models, the heat of melting of a drug would also be expected to contribute, based on arguments similar to those presented in liquid solution theory [10].

Various methods have been proposed to determine the solubility of a drug in a polymer, and have been summarized previously [11]. Some use liquid media as surrogates for solid polymers and determine the solubility of the drug in a liquid medium that is chemically similar to the polymer, such as determining the solubility of a drug in monomer/dimer liquid forms of the polymer [12,13] or drug-polymer complexation in solution [14]. Other methods include calculating or determining solubility parameters [15,16], correlating solubilities of drugs and polymers in common solvents [17], and eutectic characterizations [18,19]. Still others include characterizing the melting point depression of drug particles that are physically mixed (i.e., mixtures of particles rather than individual molecules) in a polymer [12], and determining temperatures at which phase separation is lost as a function of drug loading [20-22].

All of the above methods have shown limited success and the predicted results vary widely. In addition, methods to determine the drug solubility that involve the use of solid polymers directly are typically carried out at elevated temperatures to avoid impractically long experimental timeframes, and thus do not determine the solubility at storage temperatures. Because there is no generally accepted theory or method to relate solubility of a drug in solid polymer at one given temperature to the solubility at another temperatures, information obtained at elevated temperatures cannot be reliably used to predict solubilities in solids at lower temperatures [11]. In addition, for some drugs, working at elevated temperatures can result in chemical degradation during the solubility studies, thus introducing errors into the resulting data.

Importantly, none of these methods specifically include the molecular kinetic energy effects resulting from dispersing the drug in the solid structure. Because individual molecules move differently in different environments (e.g., vibrational patterns, etc.), the total kinetic energy of the drug and polymer molecules in a solid solution differs from the total kinetic energy of the unmixed components. It has recently been found that these kinetic energy differences can be important contributors to the drug-in-polymer solubility for many systems [11], and they should not be neglected.

Because liquids have no solid structure effects that limit molecular motion, methods to determine solubility that are used in liquid media (monomer/dimer solubility, complexation) do not reflect the kinetic energy differences associated with changing the solid that occur when forming a solid solution. In addition, complexation methods between a drug and polymer in solution are also indicative of interactions in a three component system (e.g., the drug, polymer, and solvent), which can be very different from the drug-polymer interactions in a solid without the presence of a liquid solvent.

Solubility parameter methods have also met with little success—it is known that molecules with similar solubility parameters do not always have same behavior when introduced into a polymer [8]. This is likely due, in part, to the fact that solubility parameter determinations depend only on the intermolecular attractions and repulsions, which are potential energy sources, and do not include kinetic energy contributions.

Eutectics have been widely investigated by thermal methods such as differential scanning calorimetry (DSC), and have theoretical links to interaction energies between the polymer and molecule [19], but the eutectic temperature is rarely close to storage temperatures. The temperatures determined using melting point depression methods [12] or methods that determine the temperature at which melting behavior vanishes [20-22] are typically much higher than room temperature as well. An addition concern is raised when applying equations derived from the Flory-Huggins model to melting point depression data, which assumes a uniform distribution of dissolved drug in the polymer. It can be questioned whether the diffusion of the drug on melting is fast enough to ensure such mixing—if not, local drug-polymer ratios would not be the same as the average for the formulation, which invalidate calculations of interaction parameters and solubility using melting point depression data.

All of the above methods fail to specifically account for the effects of molecular kinetic energy changes resulting from dissolving the drug in the polymer. The change in kinetic energy can be experimentally detected through the specific heat, which increases as more modes of molecular motion (vibrations, rotations, and translations) become available. Since the microscopic environment surrounding each molecule is different in a solid solution than for the unmixed components, the molecular motions and kinetic energies, and thus the heat capacities, would also be different in general [11]. While reports have been published that investigated some thermal aspects of solid solutions, most have been related to the effects of drugs on the glass transition temperature Tg [23]. However, the glass transition is not a thermodynamic transition, and using the Tg as a parameter does not provide thermodynamic or even empirical models that would allow prediction of the solubility of the drug in the polymer.

Because of this, an improved method is needed to predict or determine the solubility of a molecule such as a drug in a polymer, especially at different temperatures. The instant invention provides a method for predicting the solubility of a drug in a solid polymer matrix. In particular, the change in heat and entropy associated with making a solid solution from unmixed components is determined by the instant invention, and then used to predict the solubility of a drug in a polymer. The discussion of the instant invention that follows focuses on binary systems of one small molecule dissolved in one polymer. However, the method can be extended to systems with more types of molecules by one of ordinary skill in the art.

BRIEF DESCRIPTION OF THE DRAWINGS

FIG. 1 shows a hypothetical plot of $\Delta G_{SS}$ per gram of polymer vs. the moles of drug per gram of polymer for solid solutions of a drug in a polymer formed from the unmixed components at a given temperature. The minimum of the plot represents $\Delta\mu_1=0$, and the corresponding drug concentration represents the solubility of the drug in the polymer at that temperature.

FIG. 2 shows experimental DSC data from 220-310K for the drug indomethacin and the polymer PVP K-30 (polyvinylpyrrolidone). The indomethacin concentration is 2.5% by weight and the PVP-K30 concentration is 97.5% by weight (1 gram of indomethacin per 39 grams of PVP-K30). The solid line represents the specific heat vs. temperature experimental data for the solid solution, and the dashed line represents the specific heat data for the corresponding unmixed components. The dotted line represents the difference in specific heats (solid solution minus unmixed components), which is $\Delta C_P$.

FIG. 3 shows the difference in specific heats for indomethacin 2.5% by weight with PVP-K30. The solid line from 220-310 K represents the experimentally determined difference $\Delta C_P$ taken from FIG. 2, and the dashed line represents the fit using the function $\Delta c$ given in Example 1 and the extrapolation of $\Delta c$ to absolute zero.

FIG. 4 shows a plot of $\Delta G_{SS}$ per gram of polymer vs. the drug weight fraction for indomethacin and PVP-K30 at 25° C., as described in Example 3. The drug weight fraction corresponding to the minimum of the plot represents the drug solubility in the polymer at 25° C.

SUMMARY OF THE INVENTION

The instant invention comprises a method for predicting the solubility of a drug in a polymer, in the form of a solid solution at a given temperature. Said given temperature is not unique, and the solubility can be predicted at many temperatures using the instant invention.

The instant invention provides a method for determining the difference in specific enthalpy and specific entropy between a solid solution and its corresponding unmixed components at a given temperature or temperatures, and a method to use that information to predict the solubility of a drug in a solid polymer at the temperature(s).

In addition, the instant invention provides a method for determining the difference in specific enthalpy and specific entropy differences and predicting the drug-in-polymer solubility at given temperature(s) without requiring impractically long experiments, and without the need to perform experiments at elevated temperatures. In fact, the instant invention uses data obtained from experiments at temperatures below the temperature(s) at which the solubility is to be predicted.

In its broadest sense, the instant invention relates to determining or predicting the solubility of any molecule in any solid matrix at many temperatures. While the example and equations treat binary systems comprised of one drug plus one polymer, the examples and equations can be extended to include systems comprised of three or more components. In addition, while one of the primary advantages of the instant invention relates to use in solid matrices that exhibit significant effects of the solid structure on specific heats, the matrix is not limited to solids, but can also be a viscous liquid or semi-solid.

An important advantage of the instant invention is that, at typical storage temperatures, it provides a method for predicting the solubility that does not require the use of elevated temperatures nor impractically long experiments. While the use of elevated temperatures can allow determination of solubilities at those elevated temperatures, there is no reliable method to determine the solubility of a drug in a polymer at storage temperatures from high temperature data. In addition, performing experiments at high temperatures can accelerate chemical degradation of many drugs, thus comprising the accuracy of the experimental results.

Unlike other methods, the instant invention allows avoiding experiments at elevated temperatures that are above the temperature(s) at which the drug-in-polymer solubility is to be predicted. In fact, the experimental data needed to predict the solubility are obtained from methods such as DSC performed at temperatures that are lower than said temperature(s) at which the solubility is to be predicted.

In essence, the invention provides a method for predicting the solubility of a drug or other molecule in a solid polymer or matrix, comprising:

a) providing a drug and polymer in a specific ratio, such as grams of drug per gram of polymer;
b) determining the specific heat of the unmixed components in said ratio over a given range of temperatures;
c) making a solid solution of said drug and polymer in the same ratio as the unmixed components;
d) determining the specific heat of the solid solution over the said range of temperatures used in part (b);
e) determining the difference in specific heats between the solid solution and unmixed components over said temperature range;
f) calculating the difference in specific enthalpy and specific entropy due to specific heat differences between the solid solution and unmixed components at a given temperature;
g) calculating the specific enthalpy of mixing and specific entropy of mixing due to forming the solid solution from the unmixed components;
h) calculating the change in the specific Gibbs energy $\Delta G_{SS}$ resulting from forming the solid solution from the unmixed components;
i) repeating steps (a) through (h) for at least two other drug-polymer ratios;
j) plotting $\Delta G_{SS}$ per gram of polymer vs. the grams of drug per gram of polymer for each drug-polymer ratio at a given temperature;
k) calculating the predicted solubility of the drug in the polymer as the grams of drug per gram of polymer at which the minimum of the plot in step (j) at said given temperature.

Glossary of Terms

Matrix Polymer or other solid in which a drug is dispersed or dissolved

"0" Subscript denoting polymer or matrix
"1" Subscript denoting drug
DSC Differential scanning calorimetry
$\Delta h_{heat}$ Difference in specific enthalpy between a solid solution and unmixed components due to heat content differences
$\Delta h_{mix}$ Difference in specific enthalpy between a solid solution and unmixed components due to mixing of the drug and polymer
$\Delta s_{heat}$ Difference in specific entropy between a solid solution and unmixed components due to mixing of the drug and polymer
$\Delta s_{mix}$ Difference in specific enthalpy between a solid solution and unmixed components due to heat content differences
$\Delta g_{SS}$ Change in specific Gibbs energy when a solid solution is made from unmixed components at a given temperature
$\Delta h_{SS}$ Change in specific enthalpy when a solid solution is made from unmixed components at a given temperature
$\Delta s_{SS}$ Change in specific entropy when a solid solution is made from unmixed components at a given temperature
$\Delta \mu_{1,SS}$ The difference in chemical potential between the drug that is dissolved in a solid matrix and the pure, unmixed drug, as given by Eq. (1) and Eq. (4)
$\mu_1$ Chemical potential of the drug
"SS" Subscript denoting solid solution
P Pressure
T Temperature
$n_0$ Moles of polymer or matrix in a mixture
$n_1$ Moles of drug in a mixture
$n_{10}$ Total moles ($n_{10}=n_0+n_1$)
$w_0$ Weight of polymer or matrix in a mixture
$w_1$ Weight of drug in a mixture
$w_{10}$ Total weight in a drug-polymer mixture ($w_{10}=w_0\ w_1$)
$C_{P0}$ Specific heat of unmixed polymer or matrix
$C_{P1}$ Specific heat of unmixed drug
$C_{P10}$ Specific heat of a solid solution
$\Delta c$ Approximating function used to estimate $\Delta C_P$ at temperatures below $T_{min}$
$\Delta C_P$ Specific heat difference between a solid solution of a drug and polymer in a given ratio, and one gram of unmixed components in the same ratio, as given by Eq. (29)
$T_{min}$ Lowest temperature for which experimental thermal analysis data such as DSC is reliably obtained or used
$\phi_0$ Volume fraction of polymer in the solid solution
$\phi_1$ Volume fraction of drug in the solid solution
$M_0$ Molecular weight of polymer or matrix (g/mole)
$M_1$ Molecular weight of drug (g/mole)
$f_0$ Weight fraction of polymer or matrix in a mixture
$f_1$ Weight fraction of drug in a mixture
r Degree of polymerization
R Universal gas constant=8.314 J/K/mole
$\chi$ Drug-polymer energy interaction parameter

DISCUSSION OF THE INVENTION

Mathematical Model and Methods to Obtain Numerical Values for Terms Used in the Final Equations Solid solutions of a drug in a solid polymer or other matrix are formulated to increase the dissolution rate and bioavailability of the drug relative to that of its most stable form. However, when the dissolved drug concentration is too high, these systems are physically unstable and the dissolved drug tends to precipitate during storage. In what follows, the solubility will be characterized in terms of the chemical potential of the dissolved drug compared to the undissolved (unmixed) drug, which will then be related to the change in the specific Gibbs energy resulting from forming a solid solution. A model for determining the change in specific Gibbs energy will be presented, along with experimental and theoretical methods needed to determine it as a function of the drug loading, and a discussion of how that information can be used to predict the solubility of a drug in a solid polymer.

Role of the Chemical Potential

Parts of this section follow the presentation of Bellantone et al. [11]. It is well known that there is a thermodynamic tendency for materials to go from higher to lower chemical potential [24], which can involve a change of form, location, or both. Here, the chemical potentials to be compared will be those of the drug that is dissolved (molecularly dispersed) in a solid matrix and the drug in its precipitated or unmixed form. In this discussion, the equilibrium case will be considered in which the precipitated drug and unmixed drug will be considered as being thermodynamically interchangeable. However, it is also possible to apply the model using thermodynamic properties of metastable precipitated drug forms (forms that are not in the lowest energy, equilibrium state), in which case the apparent solubility of the metastable drug form, rather than true or equilibrium solubility of the most stable crystalline drug form would be predicted.

When a solid solution is made from unmixed components, the drug is dissolved in the polymer and the resulting change in the drug chemical potential is denoted as $\Delta\mu_{1,SS}$, where chemical potential of chemical potential of $$\Delta\mu_{1,SS} = \begin{bmatrix} \text{chemical potential of} \\ \text{drug in solid solution} \end{bmatrix} - \begin{bmatrix} \text{chemical potential of} \\ \text{unmixed or precipitated drug} \end{bmatrix} \quad (1)$$

where the subscript "1" denotes the drug and "SS" denotes solid solution.

For drug molecules that precipitate out of a solid solution, the ending form will be regions of pure precipitated drug, and $\Delta\mu_{1,SS}$ represents the difference in chemical potential between the dissolved drug form and the ending precipitated form. If a solid solution is stored for a sufficient time to allow precipitation and equilibration of the precipitated form to its most stable crystalline form, it is plausible to assume that the chemical potential of the precipitated form of the drug will equal that of the original form used to make the solid solution. (However, as noted, this is not necessary for the model presented to hold, as long as the correct chemical potential of either the starting drug material or final drug material is specified.) Also, the precipitated drug may be in the form of one or many particles, but all particles would be large enough so they take on properties of unmixed drug, in the sense that the effects of the drug-polymer molecular interactions for the precipitated drug molecules can be neglected.

For a given drug and polymer solution at a given temperature and pressure, precipitation of the dissolved drug out of a solid solution may or may not be thermodynamically favored, depending on the dissolved drug concentration. It is known from thermodynamics that as more of the drug is dissolved in the polymer, the chemical potential of the dissolved drug in the polymer increases, which leads to the following:

When the dissolved drug concentration in the polymer is lower than its solubility, $\Delta\mu_{1,SS}<0$ and precipitation is not favored, so the solid solution is stable.

When the dissolved drug concentration in the polymer is higher than its solubility, the solid solution is supersaturated, $\Delta\mu_{1,SS}>0$ and precipitation is favored, so the solid solution is unstable.

When the dissolved drug concentration in the polymer equals its solubility, the solid solution is saturated, $\Delta\mu_{1,SS}=0$ and there is no tendency to convert between dissolved and undissolved forms, so precipitation is not favored and the solid solution is stable.

The above considerations show that it is important to know the solubility, since this represents the highest stable dissolved concentration of drug in a solid solution.

Relationship Between Chemical Potential and the Gibbs Energy

When a system is changed from an initial to final state, there is an associated change in the Gibbs energy that equals the Gibbs energy of the final state minus the Gibbs energy of the initial state. For the case of making a solid solution from unmixed components with the same starting and initial temperature, this change is denoted by $\Delta G_{SS}$ and is given by $$\Delta G_{SS}=\Delta H_{SS}-T\Delta S_{SS} \quad (2)$$

where $\Delta H_{SS}$ and $\Delta S_{SS}$ denote the enthalpic and entropic changes associated with the formation of the solid solution, and T is the temperature at which $\Delta G_{SS}$ is to be evaluated.

As noted, the chemical potential of the drug plays an important theoretical role in studying solid solutions. Thermodynamically, the drug chemical potential is defined as the change in the Gibbs energy per change in amount of drug, holding all other factors constant (temperature, pressure, and the amount of polymer. This is expressed as a partial derivative of the Gibbs energy with respect to the drug content (typically in moles), given by [25]

$$\mu_1 = \left(\frac{\partial G}{\partial n_1}\right)_{T,P,n_0} \quad (3)$$

where $n_1$ and $n_0$ denote the moles of drug and polymer, respectively. For the case of making a solid solution from pure drug, the corresponding change in drug chemical potential due to making the solid solution is related to the change in the Gibbs energy by $$\Delta\mu_{1,SS} = \left(\frac{\partial \Delta G_{SS}}{\partial n_1}\right)_{T,P,n_0} \quad (4)$$

It is possible to find $\Delta\mu_{1,SS}$ in two mathematically equivalent ways. The first is to write equations for $\Delta G_{SS}$, then take the partial derivative as given by Eq. (4). The second is to plot $\Delta G_{SS}$ vs. $n_1$ (at constant of T, P and $n_0$) and take the slope at with respect to $n_1$. The first method works well if equations are known for given enthalpic or entropic contributions, while the graphing method is more practical of equations for any contribution to $\Delta G$ is not known from theoretical calculations. In practice, some contributions can be calculated theoretically while others must be determined experimentally, in which case the graphing method is likely preferable. When graphing, it is often preferable to construct plots of the change in Gibbs per amount of polymer vs. the moles of drug per amount of polymer are made, or $$\frac{\Delta G_{SS}}{w_0} \text{ vs. } \frac{n_1}{w_0} \quad (5)$$

Dividing both $\Delta G_{SS}$ and $n_1$ by the weight of the polymer in the mixture, which is proportional to the number of moles of polymer, is equivalent to holding the amount of polymer constant as required by the partial derivative given by Eq. (4). Once the plot is constructed, the slope gives $\Delta\mu_{1,SS}$. A hypothetical example is shown in FIG. 1, which shows where a solid solution is stable (negative or zero slope, corresponding to $\Delta\mu_{1,SS} \leq 0$) and where it is unstable (positive slope, corresponding to $\Delta\mu_{1,SS} > 0$) for a given temperature.

Other plots can be derived from the one described by Eq. (5), in which $\Delta G_{SS}$ or a quantity proportional to it decreases as some function of the drug concentration to a minimum and then increases, and in which the minimum of the plot can be used to identify the drug solubility. For instance, since $n_1 = w_1/M_1$, where $w_1$ denotes the weight of the drug in the formulation and $M_1$ denotes the molecular weight of the drug, the plot given by Eq. (5) can be replaced by $$\frac{\Delta G_{SS}}{w_0} \text{ vs. } \frac{w_1}{w_0} \quad (5)$$

The minimum of this plot corresponds to the drug-in-polymer solubility as grams of drug per gram of polymer. This can be related to the weight fractions of the polymer and drug in the formulation, which are denoted by $f_0$ and $f_1$ and are given as $$f_0 = \frac{w_0}{w_{10}} \quad (7)$$

$$f_1 = \frac{w_1}{w_{10}}$$

$$w_{10} = w_0 + w_1$$

Since $w_1/w_0 = f_1/f_0$ the solubility in terms of the drug fraction is also obtained from the minimum of a plot of $$\frac{\Delta G_{SS}}{w_0} \text{ vs. } f_1 \quad (8)$$

It is convenient to express the thermodynamic quantities in terms of the specific Gibbs, specific enthalpy and specific entropy, which are the Gibbs energy per gram, the enthalpy per gram, and the entropy per gram of sample, respectively. These will be denoted by lowercase g, h and s, respectively. Denoting the change in specific Gibbs energy due to forming a solid solution ($\Delta G_{SS}$ per gram) as $\Delta g_{SS}$, and noting that $$\frac{\Delta G_{SS}}{w_0} = \frac{\Delta G_{SS}/w_{10}}{w_0/w_{10}} = \frac{\Delta g_{SS}}{f_0},$$

the plot of Eq. (8) can be replaced by an alternative plot of $$\frac{\Delta g_{SS}}{f_0} \text{ vs. } f_1 \quad (9)$$

The minimum of a plot Eq. (9) will also identify the solubility of a drug in a solid polymer.

It should be noted that the solubility of a drug in a polymer depends on the temperature, and typically increases as the temperature at which the solubility is evaluated increases. Thus, the general form of the plot shown in FIG. 1 or described by Eq. (6)-(9) would still apply in the sense that the plot would show a negative slow at low drug fractions, a minimum at some drug fraction, and a positive slope at higher drug fractions. However, the exact values of the slopes and drug concentrations corresponding to the minima would be different for different temperatures. In general, it would be expected that raising the temperature at which the solubility data is evaluated would result in the minimum of the curve shifting to the right (corresponding to higher concentrations). This consideration is important, because it can be of interest to evaluate the drug-in-polymer solubility at more than one temperature.

Determining $\Delta g_{SS}$

In forming a solid solution, the initial state consists of pure precipitated or undissolved drug plus empty polymer at a given temperature, and the final state consists of a solid solution of drug dissolved in the polymer at the same temperature. It is assumed that all of the drug present goes into the solid solution, and the approach is to evaluate $\Delta g_{SS}$ for all solutions and determine the solubility as the solution at which $\Delta g_{SS}$ is minimized. (If excess drug that does not dissolve is included, it would increase the specific Gibbs energy of the initial and final states by the same amount, so neither the slopes of plots such as Eq. (5) nor the predicted solubility would not be affected.)

The Gibbs, enthalpy and entropy are thermodynamic state functions, so the change in their values depends only on the difference between the initial and final states, and not the particular process that brought about the change [25]. Also, if temperatures of the starting and final states are the same and denoted by T, it is been shown that [11]

$$\begin{bmatrix} \text{total Gibbs} \\ \text{energy change} \end{bmatrix} = \begin{bmatrix} \text{total enthalpy} \\ \text{change} \end{bmatrix} - T \begin{bmatrix} \text{total entropy} \\ \text{change} \end{bmatrix} \quad (10)$$

which is analogous to Eq. (2). Since the specific change in Gibbs energy, specific change in enthalpy and specific change in entropy are also state functions, Eq. (10) can be written using the analogous specific Gibbs energy, specific enthalpy and specific entropy.

Eq. (10) is applicable here because the solubility is determined by comparing the unmixed and solid solution states at the same temperature. For the formation of a solid solution from pure unmixed drug and polymer at a given temperature and pressure, the changes in the specific enthalpy and specific entropy arise from the following contributions.

The specific enthalpy of mixing $\Delta h_{mix}$, which reflects differences in the potential energy content per gram of the mixture due to differences in the intermolecular interaction energies.

The specific entropy of mixing $\Delta s_{mix}$, which reflects the change in entropy per gram of mixture due to mixing of the drug in the polymer.

The difference in the specific enthalpy between the solid solution and unmixed components due to differences in the heat content, which reflects differences in the kinetic energy of the molecules in the solid solution and unmixed form. This is denoted as $\Delta s_{heat}$.

The difference in specific entropy due to the differences in heat content between the solid solution and unmixed components, which is denoted by $\Delta s_{heat}$ The above contributions can be added, so the change due to making a solid solution in the specific enthalpy and specific entropy are given by $\Delta h_{SS}=\Delta h_{mix}+\Delta h_{heat}$ and $\Delta s_{SS}=\Delta s_{mix}+\Delta s_{heat}$, respectively. From Eq. (10) in terms of specific quantities, the resulting specific Gibbs energy change $\Delta g_{SS}$ is given by $$\Delta g_{SS}=\Delta h_{SS}-T\Delta s_{SS} \quad (11)$$

The specific enthalpy and specific entropy of mixing can be calculated using known equations and models. For drugs that are uniformly mixed in the polymer, equations for the enthalpy and entropy of mixing are commonly calculated using the Flory-Huggins model [6-8]. These can be converted into the specific enthalpy and specific entropy by dividing by the weight of the mixture $w_{10}$, and are given by $$\Delta h_{mix} = n_1 \phi_0 \chi RT / w_{10} \quad (12)$$

$$\Delta s_{mix} = -\frac{R}{w_{10}}[n_1 \ln\phi_1 + n_0 \ln\phi_0] \quad (13)$$

where $n_0$ and $n_1$ denote the moles of polymer and drug in the solid solution, respectively, and $\phi_0$ and $\phi_1$ denote the corresponding volume fractions of polymer and drug, respectively. The parameter $\chi$ denotes the drug-polymer energy interaction parameter (analogous to the Flory-Huggins parameter), and R is the universal gas constant.

To evaluate the above equations, values must be known for the moles of drug and polymer $n_1$ and $n_2$, the ratio of the polymer molar volume to the drug molar volume, denoted by r. These can be calculated from the weights of drug and polymer $w_1$ and $w_0$ in the solid solution, and their respective molecular weights $M_0$ and $M_0$, using known equations [8]. The moles of drug and polymer were calculated as $$n_1 = w_1/M_1 \quad n_0 = w_0/M_0 \quad (14)$$

The drug and polymer volume fractions were calculated as $$\phi_1 = \frac{n_1}{n_1 + rn_0} \quad (15)$$

$$\phi_0 = \frac{rn_2}{n_1 + rn_0} = 1 - \phi_1$$

where r is the ratio of the molar volume of the polymer to the molar volume of the drug and is commonly approximated as the degree of polymerization, or $$r \approx \text{degree of polymerization} = \frac{\text{MW polymer}}{\text{MW monomer}} \quad (16)$$

The volume fractions are not the same as weight fractions, but are be related as $$\phi_1 = \frac{\frac{f_1}{M_1}}{\left(\frac{f_1}{M_1} + \frac{rf_0}{M_0}\right)} \quad (17)$$

$$\phi_0 = \frac{\frac{rf_0}{M_0}}{\left(\frac{f_1}{M_1} + \frac{rf_0}{M_0}\right)}$$

The interaction parameter $\chi$ can be obtained from solubility parameters calculated for each drug and polymer combination using the method of van Krevelen [7] as $$\chi = \frac{v_1(\delta_1 - \delta_0)^2}{RT} + 0.34 \quad (18)$$

where $\delta_1$ and $\delta_0$ denote the solubility parameters for the drug and polymer, respectively, and $v_1$ denotes the molar volume of the drug. The factor of 0.34 was not included in the original Flory-Huggins publications, but has been introduced to improve correlations between calculated and experimental results when the predicted value of $\chi$ is less than 0.3 or so [8].

Alternative methods of determining $\chi$ have been proposed by using the melting point method [25] and solubility determined using the endpoint method [22]. These have the potential advantage of being experimentally determined, but also suffer from the disadvantage of being determined at elevated temperatures, so the values to be used at room temperature need to be estimated. However, the of method chosen to determine $\chi$ does not affect the invention itself.

The specific enthalpy and specific entropy changes due to differences in the heat content of solid solutions vs. unmixed components, $\Delta h_{heat}$ and $\Delta s_{heat}$, can be determined from experimental data using known thermodynamic equations as follows. It is known that the changes in the enthalpy at constant pressure resulting from a temperature change are related to the heat capacity, which is defined as the change in heat content per degree change in temperature. When done at a constant pressure, which corresponds to "open pan" DSC conditions, this is referred to as the constant pressure heat capacity. (For brevity, unless otherwise noted, the terms heat capacity and specific heat will refer constant pressure conditions.) The constant pressure heat capacity per gram of material is referred to as the specific heat and is denoted by $C_P$=dh/dT, where h is the specific enthalpy.

The specific heat, specific enthalpy and specific entropy are all functions of the temperature. The specific heat can be determined using thermal analysis methods such as DSC, and changes in the specific enthalpy and specific entropy due to adding or removing heat to change the temperature from $T_1$ to $T_2$ can be calculated from the specific heat as [10]

$$\delta h = \int_{T_1}^{T_2} C_P dT \quad (19)$$

$$\delta s = \int_{T_1}^{T_2} \frac{C_P}{T} dT \quad (20)$$

From thermodynamics, it is known that at absolute zero (0 K, or 0 Kelvin), there is no heat content and the entropy due to heat content also equals zero. Thus, the specific enthalpy and specific entropy content arising from adding heat to raise the temperature from absolute zero to a temperature T are given by $$h_{heat} = \int_0^T C_P dT' \qquad (21)$$

$$s_{heat} = \int_0^T \frac{C_P}{T'} dT' \qquad (22)$$

For a mixture of $w_0$ grams of a polymer with specific heat $C_{P0}$ plus $w_1$ grams of a drug with specific heat $C_{P1}$, the total specific enthalpy and specific entropy per gram of the unmixed components due to the heat content at temperature T are given by $$h_{heat} = \int_0^T \frac{(w_0 C_{P0} + w_1 C_{P1})}{w_{10}} dT' = \qquad (23)$$
$$\int_0^T (f_0 C_{P0} + f_1 C_{P1}) dT' \text{ (unmixed components)}$$

$$s_{heat} = \int_0^T \frac{(f_0 C_{P0} + f_1 C_{P1})}{T'} dT' \text{ (unmixed components)} \qquad (24)$$

where $f_0$ and $f_1$ denote the weight fractions of the polymer and drug in the mixture, respectively, and are given by Eq. (7). The specific enthalpy and specific entropy for the corresponding solid solution at the same temperature T are given by $$h_{heat} = \int_0^T C_{P10} dT' \text{ (solid solution)} \qquad (25)$$

$$s_{heat} = \int_0^T \frac{C_{P10}}{T'} dT' \text{ (solid solution)} \qquad (26)$$

where $C_{P10}$ denotes the specific heat of the solid solution. Thus, the differences between the specific enthalpy and specific entropy per gram (solid solution minus the unmixed components) are given by $$\Delta h_{heat} = \int_0^T (C_{P10} - f_1 C_{P1} - f_0 C_{P0}) dT' \qquad (27)$$

$$\Delta s_{heat} = \int_0^T \frac{(C_{P10} - f_1 C_{P1} - f_0 C_{P0})}{T'} dT' \qquad (28)$$

In practice, there is a lower limit to the temperature at which thermal analysis instruments such as DSC can provide accurate experimental data. As a result, it is not possible to experimentally obtain the necessary specific heats over all temperatures down to absolute zero, but instead they only be evaluated to a minimum temperature, denoted by $T_{min}$. The experimental data can be used to construct a temperature-dependent difference in specific heats, denoted as $\Delta C_P$, which is defined as the difference between the specific heat of the solid solution minus the specific heat of the unmixed components in the same ratio, over the temperature range of $T_{min}$ to any higher temperature T for which experimental specific heat data is available. This is given by $$\Delta C_P = C_{P10} - f_1 C_{P1} - f_2 C_{P0} \text{(from } T_{min} \text{ to } T) \qquad (29)$$

Because of the thermal analysis instrument limitations, $\Delta C_P$ provides no data between absolute zero and $T_{min}$, so it is necessary to estimate the values of specific heat differences at temperatures below $T_{min}$. One way to do this is to extrapolate the plot of the experimentally obtained $\Delta C_P$ vs. the temperature from $T_{min}$ to absolute zero. This can be done as follows.

Obtain the experimental values for $\Delta C_P$ from $T_{min}$ up to at least temperature T at which the solubility of the drug in the polymer is to be evaluated.

Construct an approximating function $\Delta c$ that is a function of the temperature, which will be used to estimate $\Delta C_P$ at temperatures lower than $T_{min}$.

Fit the function $\Delta c$ to the experimental values of $\Delta C_P$ from $T_{min}$ to T using any appropriate method, such as linear or nonlinear regression.

Using the fitted equation for $\Delta c$, calculate values of $\Delta c$ over temperatures from absolute zero to $T_{min}$. These values will be used as substitutes for experimental specific heat difference for temperatures below $T_{min}$.

There is no theoretical model or equation that dictates the mathematical form of $\Delta c$, and more than one functional form can be chosen. Possible forms for $\Delta c$ include linear forms, polynomials, logarithmic forms, exponential forms, power series, etc. It is also possible to use different forms in different temperature ranges. (For example, a polynomial above $T_{min}$, and a linear form with an intercept of zero below that temperature.) However, thermodynamic considerations require that the value of $\Delta c$ approach zero as the temperature approaches absolute zero. This is because the heat capacities of materials is zero at absolute zero, so the differences must also be zero at absolute zero. Thus, a preferred form would allow a fit of $\Delta c$ to $\Delta C_P$ and an extrapolation for which $\Delta c = 0$ at absolute zero. One preferred form would be a sum of a constant plus exponentials, such as $$\Delta c = a_0 + a_1 \exp(a_2 T) + a_3 \exp(a_4 T) + a_5 \exp(-a_6 T) + a_7 \exp(-a_8 T) \qquad (30)$$

where $a_0, a_1 \ldots a_8$ are temperature independent parameters with values that can be determined or fit by nonlinear regression or other methods so Eq. (30) will be a good approximation to the experimental $\Delta C_P$ vs. temperature data over the experimental temperature range. In such fits, the constraint that $a_0 + a_1 + a_3 + a_5 + a_7 = 0$ satisfies the condition that $\Delta c = 0$ at absolute zero.

The function $\Delta c$ will in general be different for each combination of drug and polymer. In practice, $\Delta c$ is defined by its chosen form and the fitted values of the adjustable parameters subject to the constraint that $\Delta c$ equal zero at absolute zero. Thus, even the same drug and polymer, there will in general be a distinct $\Delta c$ for each weight ratio, even if the form of $\Delta c$ does not change, due to different values of $a_0, a_1 \ldots a_8$ for each ratio.

Alternative forms of $\Delta c$ can also be used. For instance, the heat capacities of the solid solution and unmixed components can be separately obtained and fit with distinct approximating functions, which could be extrapolated separately to zero and the difference between them taken as a final step to obtain a function $\Delta c$. However, in addition to requiring that the individual extrapolated heat capacities vanish at absolute zero, an addition constraint must be imposed requiring that the slopes with respect to the temperature of both $\Delta c$ and the experimental $\Delta C_P$ at be the same. Thus, fitting the experimental $\Delta C_P$ directly is likely more convenient and preferred. However, the choice procedure to construct $\Delta c$ does not change the invention.

Using the approximating function $\Delta c$ and the experimentally obtained $\Delta C_P$ data, the final equation for the difference in enthalpy and entropy between the solid solution and unmixed components due to heat differences is given as $$\Delta h_{heat} = \int_0^{T_{min}} \Delta c \, dT' + \int_{T_{min}}^T (C_{P10} - f_1 C_{P1} - f_0 C_{P0}) dT' \quad (31)$$

$$\Delta_{heat} = \int_0^{T_{min}} \frac{\Delta c}{T'} dT' + \int_{T_{min}}^T \left( \frac{f_{10} C_{P10} - f_1 C_{P1} - f_0 C_{P0}}{T'} \right) dT' \quad (32)$$

and, from Eq. (11), the specific change in Gibbs energy is given by $$\Delta g_{SS} = \frac{n_1 \phi_0 \chi RT}{w_{10}} + \frac{RT}{w_{10}} (n_1 \ln \phi_1 + n_0 \ln \phi_0) + \quad (33)$$

$$\int_0^{T_{min}} \Delta c \, dT' + \int_{T_{min}}^T (C_{P10} - f_1 C_{P1} - f_0 C_{P0}) dT' -$$

$$T \int_0^{T_{min}} \frac{\Delta c}{T'} dT' - T \int_{T_{min}}^T \left( \frac{C_{P10} - f_1 C_{P1} - f_0 C_{P0}}{T'} \right) dT'$$

The above model and equations consider binary systems in which one drug forms a solid solution with one polymer. However, the invention is not limited to binary systems, and the equations can be extended to include ternary systems, etc. Cases can include the solubility of a drug in a polymer mixture, or the solubility of a drug in a mixture of a polymer and another dissolved molecule, which could be a drug or an excipient. In those cases, the solubility of the drug in the polymer would still be determined from the minimum of a plot of $\Delta g_{SS}/f_0$ vs. $f_1$, as prescribed by Eq. (9), with the equations used to calculate $\Delta g_{SS}$ being appropriately modified.

Many of the equations above are thermodynamic in nature, and thus most correctly apply to final states that are most thermodynamically stable (e.g., final and lowest energy states). For instance, the equations assume precipitation of drug molecules dissolved in a polymer result in the chemical potential of the precipitated drug being the same as the original undissolved crystalline form. However, as noted, the model can also be applied to metastable forms of the drug and/or polymer.

EXAMPLE 1

Determining $\Delta c$, $\Delta h_{heat}$ and $\Delta s_{heat}$ for Indomethacin 2.5% by Weight and PVP-K30 at 20° C. and 30° C.

The drug indomethacin and the polymer PVP-K30 were taken in a ratio of 2.5% indomethacin and 97.5% PVP-K30 by weight (e.g., 1 part indomethacin and 39 parts PVP-K30 by weight). DSC was performed on the pure indomethacin and pure PVP-K30, and the specific heats for the indomethacin CPI and PVP-K30 $C_{P0}$ were obtained as a function of the temperature over the range of 220K to 310K. The DSC instrument provided reliable data as low as 220K, which was taken as $T_{min}$. Solid solutions were formed by mixing the drug and polymer in a mortar and pestle, allowing them to stand at 403 K (130° C.) for 5 days, then allowing them to cool to room temperature. DSC was also performed to determine the specific heat of the solid solution $C_{P10}$ from 220K to 310K. All DSC experiments were performed using a pinhole in the lid, which approximated constant pressure conditions, so the specific heats were considered to be obtained at constant pressure. All heating and cooling rates were 5° C. per minute.

At each temperature for which experimental data was obtained, the specific heat of the unmixed components was calculated as $$\begin{bmatrix} \text{Specific heat of} \\ \text{unmixed components} \end{bmatrix} = 0.025 C_{P1} + 0.975 C_{P0}$$

and the function $\Delta C_P$ was constructed from the experimental data at each temperature as $$\Delta C_P = C_{P10} - \begin{bmatrix} \text{specific heat of} \\ \text{unmixed components} \end{bmatrix}$$

FIG. 2 shows the specific heat vs. temperature data for the unmixed components, the corresponding solid solution, and the difference of the data $\Delta C_P$, over the temperature range of 220K to 310K. The form used for $\Delta c$ was the same as that given by Eq. (30), and was fitted to the data for $\Delta C_P$ over temperature range of 220K to 310K by nonlinear regression, subject to the constraint that $a_0+a_1+a_3+a_5+a_7=0$ (which sets $\Delta c=0$ at absolute zero). The constrained fitting of $\Delta c$ to $\Delta C_P$ was done using the Solver™ function in Excel™, and the following values were obtained for the parameters: $a_0=-0.017447$, $a_1=0.147513$, $a_2=0.005839$, $a_3=0$, $a_5=-0.557832$, $a_6=0.0$, $a_7=0.427767$, and $a_8=0006406$. (The value for $a_4$ was not determined because the coefficient multiplying the exponential $a_3$ was zero. Also, $a_6$ was set to zero because its fitted value was less than $1 \times 10^{-10}$.) These values were inserted as the values for the $a_n$ in Eq. (30), so the actual function $\Delta c$ for these data was given by $$\Delta c = -0.017447 + 0.147513 \exp(0.005839T) - 0.557832 + 0.427767 \exp(-0.006406T) \quad (34)$$

Values of $\Delta c$ were calculated over temperature from zero to 220K. The fitted plot and calculated values of $\Delta c$ are shown in FIG. 3.

Using the values $\Delta c$ calculated from Eq. (34) for temperatures from 0 to 220K, and the experimental values of $\Delta C_P$, values of $\Delta h_{heat}$ and $\Delta s_{heat}$ were calculated from Eq. (31) and (32), respectively, for various temperatures. For this combination of indomethacin and PVP-K30, the calculated specific enthalpy values at −10° C. and 25° C. (263 K and 298 K) were $\Delta h_{heat}=9.66$ J/g and 18.347 J/g, respectively. The calculated specific entropy values at −10° C. and 25° C. were $\Delta s_{heat}=0.0479$ J/K/g and 0.0787 J/K/g, respectively.

EXAMPLE 2

Determining the Solubility of Indomethacin in PVP-K30 at 25° C.

The drug indomethacin and the polymer PVP-K30 were taken in various ratios, corresponding to weight percentages of indomethacin in the mixture of 2.5%, 10%, 15%, and 20%. DSC was performed on the pure indomethacin and pure PVP-K30, and the specific heat for each was obtained as a function of the temperature over the range of 220K to 310K. The DSC instrument provided reliable data as low as 220K, which was taken as $T_{min}$. Solid solutions were formed by mixing the drug and polymer in a mortar and pestle, allowing them to stand at 130° C. (403 K) for 5 days, then allowing them to cool to room temperature. DSC was also performed to determine the specific heat of the solid solutions from 220K to 300K. All DSC was performed using a pinhole in the lid and was thus considered open pan, so the specific heats were considered to be obtained at constant pressure. All heating and cooling rates were 5° C. per minute.

For each drug-polymer mixture, $\Delta C_P$ and $\Delta c$ were obtained using the procedure and functional form for $\Delta c$ described in Example 1. (For each drug-polymer ratio, separate sets of $a_0, a_1 \ldots a_8$ were obtained by the fitting.) The values of $\Delta h_{heat}$ and $\Delta s_{heat}$ were obtained at 25° C. as described in Example 1 for each drug-polymer ratio. For instance, for indomethacin 2.5% and PVP-K30, $\Delta h_{heat}$=18.347 J/g and $\Delta s_{heat}$=0.0787 J/K/g.

The entire procedure was repeated for each indomethacin-PVP combinations (2.5% m 10%, 15% and 20% indomethacin by weight), including obtaining the adjustable parameters $a_0, a_1 \ldots a_8$ for each indomethacin/PVP-K30 combination. The same molecular weights (357.8 g/mole for indomethacin 40,000 g/mole for PVP-K30), value of r (360, based on a monomer molecular weight of 111 g/mole) and interaction parameter $\chi$ (0.747 at 25° C. [11]) were used for all combinations. The values of $\Delta g_{SS}$ at 25° C. were calculated for each drug-polymer ratio from Eq. (33), and subsequently used to calculate values of $\Delta g_{SS}/f_0$.

The plot of the resulting $\Delta g_{SS}/f_0$ vs. the indomethacin weight fraction $f_1$, corresponding Eq. (9), is shown in FIG. 4. Although additional weight percentages would be used in practice to construct the plot, the plot shows that there is a minimum value of $\Delta g_{SS}/f_0$ occurring at the indomethacin weight fraction is approximately 0.15 (approximately 1 gram of indomethacin per 5.67 grams of PVP-K30, or 0.176 gram indomethacin per gram of PVP-K30). Thus, the solubility is taken as 0.176 g indomethacin per gram of PVP-K30 at 25° C. and the maximum stable weight fraction of an indomethacin in PVP-K30 solid solution is 15% by weight.

REFERENCES

1. Martin A., Swarbrick J. Cammarata A. 1983. Physical Pharmacy, Third Edition. Lea & Febiger, Chapter 7.
2. Chiou W L, Riegelman S. 1971. Pharmaceutical applications of solid dispersion systems. J Pharm Sci 60:1281-1302.
3. Simonelli A P, Mehta S C, Higuchi W I. 1969. Dissolution rates of high energy polyvinyl pyrrolidone (PVP)-sulfathiazole coprecipitates. J Pharm Sci 58: 538-549.
4. Leuner C, Dressman J. 2002. Improving drug solubility for oral delivery using solid dispersions. Eur J Pharm Biopharm 50:47-60.
5. Serajuddin A T M. 1999. Solid dispersion of poorly water-soluble drugs: Early promises, subsequent problems, and recent breakthroughs. J Pharm Sci 88:1058-1066.
6. Hildebrand J, Scott R. 1950. Solubility of Non-electrolytes, Third Edition, Rheinhold.
7. van Krevelen D W, TeNijenhuis K. 2009. Properties of Polymers, 4$^{th}$ Edition. Elsevier Scientific, Chapter 7.
8. Heimenz P C, Lodge T P. 2007. Polymer Chemistry, Second Edition. CRC Press, Chapter 7.
9. Flory P J. 1953. Principles of Polymer Chemistry. Cornell University Press, Chapter 12.
10. Y., Grant D. J. W., Brittain H. G. 2007. Principles of solubility (Chapter 1). In Solvent systems and their selection in pharmaceutics and biopharmaceutics; Augustijns P, Brewster M. E Eds. Springer-AAPS.
11. R. A. Bellantone, P. Patel, H. Sandhu, D. S. Choi, D. Singhal, H. Chokshi, A. W. Malick, N. H. Shah. A Method to Predict the Equilibrium Solubility of Drugs in Solid Polymers near Room Temperature Using Thermal Analysis. J. Pharm. Sci., 101(12), 4549-4558 (2012).
12. Marsac P J, Shamblin S L, Taylor L S. 2006. Theoretical and practical approaches for prediction of drug-polymer miscibility and solubility. Pharm Res 23:2417-2426.
13. Paudel A, Humbeeck J V, den Mooter G V. 2010. Theoretical and Experimental Investigation on the Solid Solubility and Miscibility of Naproxen in Poly(vinylpyrrolidone). Mol Phar 7: 1133-1148.
14. Velaz I, Sanches M, MartinC, Martinez-Oharriz M C, Nornoza A. 1997. Interaction of Naproxen with Vinyl Pyrrolidone and P-Cyclodextrin: a Flurometric Study. In J Pharm 150: 211-217.
15. Gupta J, Nunes C, Vyas S, Jonnalagadda S. 2011. Prediction of Solubility Parameters and Miscibility of Pharmaceutical Compounds by Molecular Dynamics Simulations. J Phys Chem B, online date Feb. 9, 2011:
16. Greenhalgh D, Williams A C, Timmins P, York P. 1999. Solubility parameters as predictors of miscibility in solid dispersions. J Pharm Sci 88: 1182-1190.
17. Pitt C G, Bao Y T, Andrady A L, Samuel P N K. 1988. The correlation of polymer-water and octanol-water partition coefficients: estimation of drug solubilities in polymers. Int J Pharm 45: 1-11.
18. Lacoulonche F, Chauvet A, Masse J, Egea M A, Garcia M L. 1998. An investigation of F B interactions with poly(ethylene glycol) 6000, poly(ethylene glycol) 4000, and poly-2-caprolactone by thermoanalytical and spectroscopic methods and modeling. J Pharm Sci 87:543-551.
19. Vippagunta, S R, Wang, Z, Hornung, S, Krill, S L. Factors Affecting the Formation of Eutectic Solid Dispersions and Their Dissolution Behavior. J. Pharm. Sci, Vol 96 (2), 2007, 294-304.
20. Vasanthavada M, Tong W, Joshi Y, Kislalioglu M S. 2004. Phase behavior of amorphous molecular dispersions I: Determination of the degree and mechanism of solid solubility. Pharm Res 21: 1598-1606.
21. Vasanthavada M, Tong W, Joshi Y, Kislalioglu M S. 2004. Phase behavior of amorphous molecular dispersions II: Role of hydrogen bonding in solid solubility and phase separation kinetics. Pharm Res 22:440-448.
22. Sun Y, Tao J, Zhang G G Z, Yu L. 2010. Solubilities of Crystalline Drugs in Polymers: An Improved Analytical Method and Comparison of Solubilities of Indomethacin and Nifedipine in PVP, PVP/VA, and PVAc. J Pharm Sci 99: 4023-4031.
23. Hancock B C, Shamblin S L, Zografi G. 1995. Molecular Mobility of Amorphous Pharmaceutical Solids Below Their Glass Transition Temperatures. Pharm Res 12: 799-806.
24. Callen H. 1985. Thermodynamics and an Introduction to Thermostatistics. Wiley, Chapter 2.
25. Klotz I M, Rosenberg R M. 1974. Chemical Thermodynamics—Basic Theory and Methods, Third Edition. Benjamin-Cummings, Chapter 2.
26. Marsac P J, Li T, Taylor L S. 2008. Estimation of drug—polymer miscibility and solubility in amorphous solid dispersions using experimentally determined interaction parameters. Pharm Res 26:139-151.

I claim:

1. A method for determining the difference in specific entropies at a given temperature T and pressure due to heat content differences between a solid solution and unmixed components of the same composition, comprising
    a) providing unmixed components of a substance and a polymer in a known weight ratio and at a given temperature;

b) providing a solid solution mixture of said substance in said polymer in the same weight ratio at said temperature;
c) obtaining the specific heats of said unmixed components using DSC or other appropriate method, from the lowest temperature for which data is used $T_{min}$ to said temperature T or higher;
d) obtaining the specific heat of said solid solution using DSC or other appropriate method, from the lowest temperature for which data is used $T_{min}$ to said temperature T or higher;
e) taking the difference between the specific heats of said solid solution and said unmixed components over the experimental range from $T_{min}$ to said temperature T or higher to construct a function $\Delta C_p$;
f) providing an approximating function $\Delta c$ that fits said experimental $\Delta C_p$ data;
g) calculating values of $\Delta c$ for temperatures ranging from absolute zero to $T_{min}$ and
h) determining the difference in specific entropy due to the heat content difference $\Delta S_{heat}$ between said solid solution and said unmixed components from Eq. (32).

2. A method for determining the difference in entropies at a given temperature T and pressure due to heat content differences between a solid solution and unmixed components of the same composition, comprising
a) providing unmixed components of a substance that is crystalline and a polymer in a known weight ratio and at a given temperature;
b) providing a solid solution mixture of said substance in said polymer in the same weight ratio at said temperature;
c) obtaining the specific heats of said unmixed components using DSC or other appropriate method, from the lowest temperature for which data is used $T_{min}$ to said temperature T or higher;
d) obtaining the specific heat of said solid solution using DSC or other appropriate method, from the lowest temperature for which data is used $T_{min}$ to said temperature T or higher;
e) taking the difference between the specific heats of said solid solution and said unmixed components over the experimental range from $T_{min}$ to said temperature T or higher to construct a function $\Delta C_p$;
f) providing an approximating function $\Delta c$ that fits said experimental $\Delta C_p$ data;
g) calculating values of $\Delta c$ for temperatures ranging from absolute zero to $T_{min}$ and
h) determining the difference in specific entropy due to the heat content difference $\Delta S_{heat}$ between said solid solution and said unmixed components from Eq. (32).

3. A method for determining the difference in entropies at a given temperature T and pressure due to heat content differences between a solid solution and unmixed components of the same composition, comprising
a) providing unmixed components of a substance that is amorphous and a polymer in a known weight ratio and at a given temperature;
b) providing a solid solution mixture of said substance in said polymer in the same weight ratio at said temperature;
c) obtaining the specific heats of said unmixed components using DSC or other appropriate method, from the lowest temperature for which data is used $T_{min}$ to said temperature T or higher;
d) obtaining the specific heat of said solid solution using DSC or other appropriate method, from the lowest temperature for which data is used $T_{min}$ to said temperature T or higher;
e) taking the difference between the specific heats of said solid solution and said unmixed components over the experimental range from $T_{min}$ to said temperature T or higher to construct a function $\Delta C_p$;
f) providing an approximating function $\Delta c$ that fits said experimental $\Delta C_p$ data;
g) calculating values of $\Delta c$ for temperatures ranging from absolute zero to $T_{min}$ and
h) determining the difference in specific entropy due to the heat content difference $\Delta S_{heat}$ between said solid solution and said unmixed components from Eq. (32).

* * * * *